United States Patent
Guo

(10) Patent No.: US 12,110,332 B2
(45) Date of Patent: Oct. 8, 2024

(54) BIFUNCTIONAL FUSION PROTEIN TARGETING CD47 AND PD-L1

(71) Applicant: Taizhou Mabtech Pharmaceutical Co., Ltd., Jiangsu (CN)

(72) Inventor: Yajun Guo, Shanghai (CN)

(73) Assignee: Taizhou Mabtech Pharmaceutical Co., Ltd., Jiangsu (CN)

( * ) Notice: Subject to any disclaimer, the term of this patent is extended or adjusted under 35 U.S.C. 154(b) by 471 days.

(21) Appl. No.: 16/765,008

(22) PCT Filed: Nov. 20, 2017

(86) PCT No.: PCT/CN2017/111828
§ 371 (c)(1),
(2) Date: May 18, 2020

(87) PCT Pub. No.: WO2019/095358
PCT Pub. Date: May 23, 2019

(65) Prior Publication Data
US 2020/0354458 A1    Nov. 12, 2020

(51) Int. Cl.
| | | |
|---|---|---|
| C07K 16/28 | (2006.01) |
| A61K 39/00 | (2006.01) |
| A61P 35/00 | (2006.01) |
| A61P 37/02 | (2006.01) |
| C07K 14/705 | (2006.01) |

(52) U.S. Cl.
CPC .......... *C07K 16/2827* (2013.01); *A61P 35/00* (2018.01); *A61P 37/02* (2018.01); *C07K 14/70503* (2013.01); *C07K 16/2896* (2013.01); *A61K 2039/505* (2013.01); *C07K 16/2803* (2013.01); *C07K 2317/31* (2013.01); *C07K 2317/51* (2013.01); *C07K 2317/515* (2013.01); *C07K 2317/52* (2013.01); *C07K 2317/732* (2013.01); *C07K 2319/70* (2013.01)

(58) Field of Classification Search
None
See application file for complete search history.

(56) References Cited

U.S. PATENT DOCUMENTS

| | | | | |
|---|---|---|---|---|
| 8,597,911 B2* | 12/2013 | Miyazaki | ........... | C07K 16/2866 435/69.7 |
| 9,447,159 B2* | 9/2016 | Ast | ..................... | C07K 16/3007 |
| 10,035,855 B2* | 7/2018 | Swanson | ................. | A61P 11/06 |
| 10,059,769 B2* | 8/2018 | Fang | ....................... | A61P 31/04 |
| 11,634,490 B2* | 4/2023 | Lin | ..................... | C07K 16/2803 424/133.1 |
| 11,672,859 B2* | 6/2023 | Tian | ................... | A61K 38/1774 424/136.1 |
| 2010/0203056 A1* | 8/2010 | Irving | ..................... | A61P 43/00 435/69.6 |
| 2016/0229913 A1* | 8/2016 | Bosques | ................ | C07K 16/46 |
| 2017/0107270 A1* | 4/2017 | Pons | .................. | A61K 47/6811 |

FOREIGN PATENT DOCUMENTS

| | | | |
|---|---|---|---|
| CN | 105073780 A | | 11/2015 |
| CN | 106519036 A | | 3/2017 |
| CN | 107108748 A | | 8/2017 |
| CN | 107459578 A | | 12/2017 |
| WO | WO 2016/024021 | * | 2/2016 |
| WO | 2016187226 A1 | | 11/2016 |
| WO | 2016196298 A1 | | 12/2016 |
| WO | 2017027422 A1 | | 2/2017 |

OTHER PUBLICATIONS

Merchant et al., An Efficient Route to Human Bispecific IgG, Nature Biotechnology, 1998, 16:677-681.

* cited by examiner

*Primary Examiner* — Marianne P Allen
(74) *Attorney, Agent, or Firm* — Quarles & Brady LLP

(57) ABSTRACT

A bifunctional fusion protein targeting CD47 and PD-L1, which belongs to the field of biomedicine and solves the problems that anti-PD-1/PD-L1 treatment has poor effect on low immunogenic tumors and anti-CD47 treatment has poor targeting properties. The fusion protein consists of a CD47-binding moiety and a PD-L1-binding moiety linked by means of a disulfide bond, can block both the binding of CD47 to SIRPa and the binding of PD-L1 to PD-1, not only activating macrophage phagocytosis of tumor cells and promoting antigen presentation in innate immunity, but also promoting tumor-specific T cell activation in acquired immunity, and has lower hematological toxicity. The fusion protein has better anti-tumor efficacy and hematological safety than anti-PD-L1 or anti-CD47 therapy alone, and animals from which a tumor has disappeared after the treatment of the fusion protein produce immunity against re-inoculation of the same tumor cell.

2 Claims, 6 Drawing Sheets
Specification includes a Sequence Listing.

SEQUENCE LISTING

```
<160> NUMBER OF SEQ ID NOS: 10

<210> SEQ ID NO 1
<211> LENGTH: 350
<212> TYPE: PRT
<213> ORGANISM: Artificial Sequence
<220> FEATURE:
<223> OTHER INFORMATION: synthetic

<400> SEQUENCE: 1

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Glu Pro Lys Ser Ser Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Cys Thr Leu Pro Pro
                245                 250                 255

Ser Arg Asp Glu Leu Thr Lys Asn Gln Val Ser Leu Ser Cys Ala Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
```

```
                290                 295                 300
Gly Ser Phe Phe Leu Val Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
                340                 345                 350
```

<210> SEQ ID NO 2
<211> LENGTH: 214
<212> TYPE: PRT
<213> ORGANISM: Artificial Sequence
<220> FEATURE:
<223> OTHER INFORMATION: Light Chain Amino acid sequence of the PD-L1
      binding moiety of the bifunctional fusion protein

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 3
<211> LENGTH: 448
<212> TYPE: PRT
<213> ORGANISM: Artificial Sequence
<220> FEATURE:
<223> OTHER INFORMATION: Heavt Chain Amino acid sequence of the PD-L1
      binding moiety of the bifunctional fusion protein

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
```

```
                20                  25                  30
Trp Ile His Trp Val Arg Gln Ala Pro Gly Lys Gly Leu Glu Trp Val
             35                  40                  45
Ala Trp Ile Ser Pro Tyr Gly Gly Ser Thr Tyr Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Arg His Trp Pro Gly Gly Phe Asp Tyr Trp Gly Gln Gly Thr
                100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Cys Arg Asp Glu Leu Thr Lys Asn Gln Val Ser Leu Trp Cys
            355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445
```

<210> SEQ ID NO 4
<211> LENGTH: 1053
<212> TYPE: DNA
<213> ORGANISM: Artificial Sequence
<220> FEATURE:
<223> OTHER INFORMATION: Nucleotide coding sequence of the CD47 binding
      moiety of the bifunctional fusion protein

<400> SEQUENCE: 4

```
gaagaagaac tgcagatcat ccagccggac aaatctgttt ctgttgcggc gggtgaatct      60
gcgatcctgc actgcaccat cacctctctg ttcccggttg gtccgatcca gtggttccgt    120
ggtgcgggtc cggcgcgtgt tctgatctac aaccagcgtc agggtccgtt cccgcgtgtt    180
accaccgttt ctgaaaccac caaacgtgaa aacatggact ctctatatctc tatctctaac    240
atcaccccgg cggacgcggg cacctactac tgcatcaaat ccgtaaaagg ttctccggac    300
accgaattta aatctggtgc gggcaccgaa ctgtctgttc gtgcgaaacc gtctgagccc    360
aaatcttctg acaaaactca cacatgccca ccgtgcccag cacctgaact cctggggggga    420
ccgtcagtct tcctcttccc cccaaaaccc aaggacaccc tcatgatctc ccggaccccct    480
gaggtcacat gcgtggtggt ggacgtgagc cacgaagacc ctgaggtcaa gttcaactgg    540
tacgtggacg gcgtggaggt gcataatgcc aagacaaagc cgcgggagga gcagtacaac    600
agcacgtacc gtgtggtcag cgtcctcacc gtcctgcacc aggactggct gaatggcaag    660
gagtacaagt gcaaggtctc caacaaagcc ctcccagccc ccatcgagaa aaccatctcc    720
aaagccaaag gcagccccg agaaccacag gtgtgcaccc tgcccccatc ccgggatgag    780
ctgaccaaga accaggtcag cctgtcctgc gccgtcaaag gcttctatcc cagcgacatc    840
gccgtggagt gggagagcaa tgggcagccg gagaacaact acaagaccac gcctcccgtg    900
ctggactccg acggctcctt cttcctcgtg agcaagctca ccgtggacaa gagcaggtgg    960
cagcagggga acgtcttctc atgctccgtg atgcatgagg ctctgcacaa ccactacacg   1020
cagaagagcc tctccctgtc cccgggtaaa tga                                1053
```

<210> SEQ ID NO 5
<211> LENGTH: 645
<212> TYPE: DNA
<213> ORGANISM: Artificial Sequence
<220> FEATURE:
<223> OTHER INFORMATION: Nucleotide coding sequence of the light chain
      of the PD-L1 binding moiety of the bifunctional fusion protein

<400> SEQUENCE: 5

```
gatatacaga tgacccagag cccatcttct ctcagcgcat ctgtgggcga ccgtgtcacc     60
atcacttgtc gtgccagtca ggacgtctcc actgccgtcg cctggtacca acagaagcct    120
gggaaggcgc caaaactgtt aatctactcc gctagttttc tctacagcgg tgtgccatcc    180
aggttcagcg gttctgggtc gggcacagat tttaccctga ccatcagctc tctccagcct    240
gaggacttcg ctacctacta ttgtcagcag tacttgtacc ccctgctac cttcggccag    300
gggacaaagg tggagatcaa gcgcacagtc gctgcccctt ccgtgttcat ttttcctccc    360
tctgacgagc agctaaagag cggtaccgct tcagtcgtgt gtttactgaa caactttttac    420
cctcgggaag ccaaggtcca gtggaaggtt gacaacgcac tccagtccgg caattcgcag    480
gagtctgtta ccgagcaaga ctccaaggac agcacatact ccctttcatc aactttgacg    540
ttgtctaagg ctgactacga aagcataaaa gtgtatgctt gcgaggtgac acatcagggc    600
```

```
ctgagttccc cagttaccaa atcattcaat cggggggaat gctga                    645
```

<210> SEQ ID NO 6
<211> LENGTH: 1347
<212> TYPE: DNA
<213> ORGANISM: Artificial Sequence
<220> FEATURE:
<223> OTHER INFORMATION: Nucleotide coding sequence of the heavy chain
      of the PD-L1 binding moiety of the bifunctional fusion protein

<400> SEQUENCE: 6

```
gaagtacagc tggtcgagag tggcgggggg ttggtgcagc ccggagggtc cctgcggctg      60
agttgcgccg cctccgggtt taccttctcc gactcttgga ttcactgggt gcgacaggcc     120
cctgggaaag gtctcgaatg ggtggcttgg atcagcccct acggcggatc aacctattat     180
gctgattccg tgaaggggcg cttcaccata tctgccgaca ccagtaaaaa cacagcttac     240
ctccagatga actccctgag agcagaggat actgccgtct attattgtgc cagaaggcac     300
tggccgggcg gctttgatta ctgggggcag ggcacccctcg tgaccgtgtc atctgctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcacccca gacctacatc     600
tgcaacgtga atcacaagcc cagcaacacc aaggtggaca gaaagttgag cccaaatctt     660
tgtgacaaaa ctcacacatg cccaccgtgc ccagcacctg aactcctggg gggaccgtca     720
gtcttcctct tcccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca agccgcggg aagagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catgccggga tgagctgacc    1080
aagaaccagg tcagcctgtg tgtgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctcccgg taaatga                                         1347
```

<210> SEQ ID NO 7
<211> LENGTH: 350
<212> TYPE: PRT
<213> ORGANISM: Artificial Sequence
<220> FEATURE:
<223> OTHER INFORMATION: amino acid sequence of control SIRPalpha-m-Fc'
      fusion protein

<400> SEQUENCE: 7

```
Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45
```

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser Glu Pro Lys Ser Ser Asp Lys Thr His Thr
                115                 120                 125

Cys Pro Pro Cys Pro Ala Pro Glu Leu Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
                180                 185                 190

Lys Pro Arg Glu Glu Gln Tyr Asn Ser Thr Tyr Arg Val Val Ser Val
                195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
                260                 265                 270

Lys Gly Phe Tyr Pro Ser Asp Ile Ala Val Glu Trp Glu Ser Asn Gly
                275                 280                 285

Gln Pro Glu Asn Asn Tyr Lys Thr Thr Pro Pro Val Leu Asp Ser Asp
                290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
                340                 345                 350

<210> SEQ ID NO 8
<211> LENGTH: 448
<212> TYPE: PRT
<213> ORGANISM: Artificial Sequence
<220> FEATURE:
<223> OTHER INFORMATION: amino acid sequence of heavy chain of control
      anti-PDL1

<400> SEQUENCE: 8

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Ser
                 20                  25                  30

Trp Ile His Trp Val Arg Gln Ala Pro Gly Lys Gly Leu Glu Trp Val
             35                  40                  45

Ala Trp Ile Ser Pro Tyr Gly Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ala Arg Arg His Trp Pro Gly Gly Phe Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 9
<211> LENGTH: 1053
<212> TYPE: DNA
<213> ORGANISM: Artificial Sequence
<220> FEATURE:

<223> OTHER INFORMATION: nucleotide coding sequence of control
SIRPalpha-m-Fc' fusion protein

<400> SEQUENCE: 9

```
gaagaagaac tgcagatcat ccagccggac aaatctgttt ctgttgcggc gggtgaatct      60
gcgatcctgc actgcaccat cacctctctg ttcccggttg gtccgatcca gtggttccgt     120
ggtgcgggtc cggcgcgtgt tctgatctac aaccagcgtc agggtccgtt ccgcgtgtt      180
accaccgttt ctgaaaccac caaacgtgaa acatggact tctctatctc tatctctaac      240
atcaccccgg cggacgcggg cacctactac tgcatcaaat ccgtaaagg ttctccggac      300
accgaattta atctggtgc gggcaccgaa ctgtctgttc gtgcgaaacc gtctgagccc      360
aaatcttctg acaaaactca cacatgccca ccgtgcccag cacctgaact cctgggggga     420
ccgtcagtct tcctcttccc cccaaaaccc aaggacaccc tcatgatctc ccggaccct     480
gaggtcacat gcgtggtggt ggacgtgagc cacgaagacc ctgaggtcaa gttcaactgg     540
tacgtggacg gcgtggaggt gcataatgcc aagacaaagc cgcgggagga gcagtacaac     600
agcacgtacc gtgtggtcag cgtcctcacc gtcctgcacc aggactggct gaatggcaag     660
gagtacaagt gcaaggtctc caacaaagcc ctcccagccc ccatcgagaa aaccatctcc     720
aaagccaaag gcagccccg agaaccacag gtgtacaccc tgcccccatc ccgggatgag     780
ctgaccaaga accaggtcag cctgacctgc ctggtcaaag cttctatcc agcgacatc      840
gccgtggagt gggagagcaa tgggcagccg gagaacaact acaagaccac gcctcccgtg     900
ctggactccg acggctcctt cttcctctac agcaagctca ccgtggacaa gagcaggtgg     960
cagcagggga acgtcttctc atgctccgtg atgcatgagg ctctgcacaa ccactacacg    1020
cagaagagcc tctccctgtc cccgggtaaa tga                                 1053
```

<210> SEQ ID NO 10
<211> LENGTH: 1347
<212> TYPE: DNA
<213> ORGANISM: Artificial Sequence
<220> FEATURE:
<223> OTHER INFORMATION: nucleotide coding sequence of the heavy chain
of control anti-PDL1

<400> SEQUENCE: 10

```
gaggtgcagc tggtggagtc cggcggcggc ctggtgcagc ccggcggctc cctgcggctg      60
tcctgcgccg cctccggctt caccttctcc gactcctgga tccactgggt gcggcaggcc     120
cccggcaagg gcctggagtg ggtggcctgg atctccccct acggcggctc cacctactac     180
gccgactccg tgaagggccg gttcaccatc tccgccgaca cctccaagaa caccgcctac     240
ctgcagatga actccctgcg ggccgaggac accgccgtgt actactgcgc ccggcggcac     300
tggcccggcg gcttcgacta ctggggccag ggcaccctgg tgaccgtgtc ctccgcctcc     360
accaagggcc cctccgtgtt ccccctggcc cctcctcca gtccaccctc ggcggcacc      420
gccgccctgg gctgcctggt gaaggactac ttccccgagc ccgtgaccgt gtcctggaac     480
tccggcgccc tgacctccgg cgtgcacacc ttccccgccg tgctgcagtc ctccggcctg     540
tactccctgt cctccgtggt gaccgtgccc tcctcctccc tgggcaccca gacctacatc     600
tgcaacgtga accacaagcc ctccaacacc aaggtggaca agaaggtgga gcccaagtcc     660
tgcgacaaga cccacacctg ccccccctgc cccgccccg agctgctggg cggcccctcc     720
gtgttcctgt tccccccaa gcccaaggac accctgatga tctcccggac ccccgaggtg     780
acctgcgtgg tggtggacgt gtcccacgag gaccccgagg tgaagttcaa ctggtacgtg     840
```

```
gacggcgtgg aggtgcacaa cgccaagacc aagcccggg aggagcagta cgcctccacc    900
taccgggtgg tgtccgtgct gaccgtgctg caccaggact ggctgaacgg caaggagtac    960
aagtgcaagg tgtccaacaa ggccctgccc gcccccatcg agaagaccat ctccaaggcc   1020
aagggccagc cccgggagcc ccaggtgtac accctgcccc cctcccggga ggagatgacc   1080
aagaaccagg tgtccctgac ctgcctggtg aagggcttct acccctccga catcgccgtg   1140
gagtgggagt ccaacggcca gcccgagaac aactacaaga ccaccccccc cgtgctggac   1200
tccgacggct ccttcttcct gtactccaag ctgaccgtgg acaagtcccg gtggcagcag   1260
ggcaacgtgt tctcctgctc cgtgatgcac gaggccctgc acaaccacta cacccagaag   1320
tccctgtccc tgtcccccgg caagtga                                      1347
```

BIFUNCTIONAL FUSION PROTEIN TARGETING CD47 AND PD-L1

CROSS-REFERENCE TO RELATED APPLICATIONS

This application represents the U.S. national stage entry of International Application No. PCT/CN2017/111828 filed Nov. 20, 2017, the disclosure of which is incorporated herein by reference in its entirety and for all purposes.

REFERENCE TO A SEQUENCE LISTING SUBMITTED VIA EFS-WEB

The content of the ASCII text file of the sequence listing named "850766_00087_ST25.txt" which is 24,100 bytes in size was created on Apr. 28, 2020 and electronically submitted via EFS-Web herewith the application is incorporated herein by reference in its entirety.

TECHNICAL FIELD

The disclosure belongs to the field of biomedicine, more specifically, relates to a recombinant fusion protein targeting CD47 molecules and PD-L1 molecules.

BACKGROUND OF THE DISCLOSURE

The "immune escape" of cancer cells is believed to be the primary mechanism for tumor onset, development, and drug resistance. Tumors generally protect themselves from the removal of immune systems by directly or indirectly inhibiting the signal of T cells. Tumor immune checkpoint therapy is a class of therapeutic methods for improving anti-tumor immune responses by modulating T cell activity through a series of pathways, such as co-inhibition or co-stimulation signals.

The immune checkpoint plays an important role in regulating the amplitude and duration of the T-cell response and maintaining self-tolerance by co-stimulating and co-inhibiting molecules in the immune response process and generating "on" or "off" immune response signal, preventing damage to its own tissue. Currently discovered immune check point molecules include PD-1/PD-L1, CD47/SIRPa, CTLA-4/CD80/CD86, etc.

(1) PD-1/PD-L1

PD-1 (Programmed Cell Death Protein 1) is a cell surface receptor expressed on the surface of T cells and the pre-B cells, upregulated on activated T cells, capable of binding to both PD-L1 and PD-L2 ligands. The PD-1 is an immune checkpoint protein with a negative regulation function, can prevent the activation of T cells, and plays an important role in reducing auto-immunity and promoting immune tolerance. The function of PD-1 is achieved by two pathways, one to promote apoptosis of antigen-specific T cells in lymph nodes, the other to reduce apoptosis of regulatory T cells (Treg, also called inhibitory T cells).

PD-L1 (Programmed Death-Ligand 1) is one of the ligands of PD-1, also is a transmembrane protein, primarily expressed in placenta, heart, liver, lung, kidney, skeletal muscle and limited hematopoietic tissues, as well as some leukemia cell lines. PD-L1 binds to PD-1 to form a receptor-ligand complex and emit an inhibitory signal, including inducing the generation of IL-10 (inflammation and immunosuppressive factor), down-regulating anti-apoptotic gene bcl-2 to promote apoptosis of antigen-specific T cells, and inhibiting the proliferation of CD8+ T cells in lymph nodes, etc. PD-L1 is related to the inhibition of immune systems in some special situations, such as pregnancy, tissue transplantation, autoimmune disease, hepatitis, etc. PD-L1 can also bind to CD80 with a weaker affinity ($K_D$ value of 1.4 µM) besides being able to bind to PD-1 with a stronger affinity ($K_D$ value 770 nM).

PD-L1 is found to be expressed on a variety of tumor cell surfaces so that tumor cells escape the killing of the immune system, and therefore can be used as targets for anti-tumor immunotherapy.

(2) CD47/SIRPα

CD47 (leukocyte surface antigen 47), also called as integrin-associated protein (IAP), is a transmembrane protein, associated with membrane integrins, also binds to Thrombospondin-1 (TSP-1), Signal regulatory protein alpha (SIRPa). CD47 is widely expressed on human somatic cells and overexpressed on various tumor cells, participating in various cell activities such as apoptosis, proliferation, adhesion, migration and the like.

SIRP-alpha is a trans-membrane receptor glycoprotein, specifically expressed on the surface of myeloid cells such as macrophages, dendritic cells, has a negative regulation effect on immunization, and is capable of inhibiting phagocytosis and T cell activation after binding with CD47.

CD47 binds to the SIRPa and issues a "Don'T Eat Me" signal to the immune system. Such mechanism can protect the normal cells of the human body from being killed by the immune system. But such mechanism can also be utilized by tumor cells to achieve immune escape.

A number of immune check point drugs, such as Ipilimumab (anti-CTLA-4), Nivolumab (anti-PD-1), Pembrolizumab (anti-PD-1), Atezolizumab (anti-PD-L1), Avelumab (anti-PD-L1), Durvalumab (anti-PD-L1) are currently approved for sale by the European or American Drug Administration.

However, the following problems still exist in the immune check point drugs:

Since the PD-1/PD-L1 signal pathway acts only at the effect-phase of T cells, the affecting of anti-PD-1/PD-L1 drug requires the presentation of tumor antigens, which will be clinically ineffective for about 70% of low immunogenicity tumors, and needs to be used in combination with chemotherapy, radiation therapy and Mabs; Meanwhile, cancer cells can sometimes achieve immune escape through different pathways or routes, simple blockage of the PD-1/PD-L1 pathway may be inutile to the immune escape of some cancer cells.

Antibodies targeted to CD47 have functions such as activating macrophages, enhancing T cell antigen presentation, and the like, and are functionally complementary to anti-PD-1/PD-L1. However, the expression of CD47 is not strictly tumor specific, and it is also expressed on the surface of healthy red blood cells. The tumor cell surface CD47 expression is only 3.3 times higher than normal cells. Therefore, in vivo use of CD47 antibody will often cause undesirable reaction such as anemia. To reduce side effects, a SIRPa mutant with high affinity to CD47 can only be administered as immune booster, in combination with other antibodies in the form of monomer without Fc.

If the effectiveness of the anti-PD-1/PD-L1 drug on the low immunogenicity heavy chain can be improved, and/or the blood toxicity of the CD47 targeting drug can be reduced, it will have great significance on improving the therapeutical effect on malignant tumors.

SUMMARY OF THE INVENTION

A medicine is provided in the disclosure, said medicine combines the effects of two immune checkpoint drugs (anti-PD-1/PD-L1 and anti-CD47/SIRPa) at different stages of anti-tumor immunization, forms a synergistic effect, generates higher efficacy and stronger therapeutical effect than that of a single medicine, thus improving the targeting property of the medicine to tumor cells, reducing the blood toxicity, and solving the insufficiency of the therapeutical effect or safety of the existing immune checkpoint medicine.

In particular, the disclosure provides a bifunctional fusion protein targeting CD47 and PD-L1, which can bind to PD-L1 to block PD-1/PD-L1 signaling pathway, and also can bind to CD47 to block CD47/SIRPa signaling pathway, have good cancer cell targeting and cytotoxicity (such as ADCC and CDC), and solve the problems on therapeutical effect and safety of the existing immune checkpoint antibody drugs.

The disclosure also provides a method for reducing the toxicity of the CD47-targeting drug, which can reduce side reactions such as anemia caused by the binding of the CD47-targeting drug with red blood cells.

The technical solutions of the present disclosure are as follows:

A bifunctional fusion protein targeting CD47 and PD-L1, which can bind to both CD47 molecule and PD-L1 molecule.

The fusion protein described above (designated as IAB) consists of two moieties linked by disulfide bonds (FIG. 2), wherein one can bind to CD47, formed by linking SIRPa high affinity mutant (designated as SIRPa-m) to an antibody Fc segment (designated as SIRPa-m-Fc); the other can bind to PD-L1, formed by linking a light chain (designated as anti-PDL1-L) and a heavy chain (designated as anti-PDL1-H) of anti-PD-L1 antibody by disulfide bond.

Both the antibody Fc segments contained in SIRPa-m-Fc and anti-PDL1-H peptide chains are IgG types, preferably IgG1 subtypes; To avoid the formation of unnecessary homologous dimers in the recombinant expression process of the IAB, a Knob-in-Hole structure is introduced into the Fc segments of the SIRPa-m-Fc and the anti-PDL1-H peptide chains. The "Knob-in-Hole structure" can be achieved by the following: introducing 2 amino acid mutations into the Fc segment of the anti-PDL1-H peptide chain (T366W, S354C) (based on the IgG innate sequence), forming protruded Knob structure. 4 amino acid mutations (Y349C, T366S, L368A, and Y407V) are introduced based on the IgG innate sequence into the Fc segment of the SIRPα-m-Fc peptide chains to form recessed Hole structure, and homologous pairing is prevented by a steric hindrance effect (the EU numbering system of Kabat is used for the above Fc segment amino acid mutation site, i.e., the EU numbering scheme).

More specifically, the SIRPα-m-Fc peptide chain has the amino acid sequence as set forth in SEQ ID NO: 1; the anti-PDL1-L peptide chain has the amino acid sequence as set forth in SEQ ID NO: 2, and the anti-PDL1-H peptide chain has the amino acid sequence as set forth in SEQ ID NO: 3.

The IABs can be expressed by genetically engineered CHO (Chinese hamster ovary) cells. Particularly, IABs are expressed by CHO-K1 cells, and the expression vector used is pcDNA3.1(+). The SIRPα-m-Fc is encoded by the nucleotide sequence as set forth in SEQ ID NO: 4; the light chain of the anti-PDL1-L is encoded by the nucleotide sequence as set forth in SEQ ID NO: 5; the anti-PDL1-H is encoded by the nucleotide sequence as set forth in SEQ ID NO: 6, SEQ ID NO: 5 and SEQ ID NO: 6 are inserted by genetic recombination into open reading frame (ORF) of the pcDNA3.1(+), using the constructed expression vector containing the target protein coding sequence to transfect CHO-K1 cells, then screening to obtain the cell strains capable of stably expressing the IAB for the expression of IAB.

The above-mentioned bifunctional fusion protein targeting CD47 and PD-L1 can be used for manufacturing tumor drugs and immunoregulation drugs.

Antibodies are produced by the immune system of the body stimulated by antigens. Antibodies are immunoglobulins produced by plasma cell differentiated from B lymphocytes. An antibody is capable of carrying out specific binding reaction with corresponding antigen. Antibodies can also be prepared by in vitro methods such as hybridoma, genetic engineering and the like. According to physical and chemical properties and biological functions, the antibodies can be divided into 5 categories, that is, IgM, IgG, IgA, IgE, and IgD. The IgG (Immunoglobulin G) antibody is the major antibody component in serum, adding up to about 75% of the serum immunoglobulins, and is also the primary type of existing antibody drug inside China and abroad.

Typically, a complete IgG-type antibody consists of four peptide chains (FIG. 1), including symmetrically two heavy chains and two light chains, and linked together by disulfide bonds. Each light chain consists of variable regions (VLs) and constant regions (CLs), and the heavy chain consists of variable regions (VHs) and constant regions (CHs). The heavy chain constant regions of the IgG-type antibody can be divided into three parts: CH1, CH2, and CH3. The variable regions (VLs and VHs) of the light chain and heavy chain are the moieties binding to the antigen, and the heavy chain CH2, CH3 regions have immune effecting functions such as binding to complement, Fc receptor, protein A, and induces ADCC (antibody dependent cell-mediated cytotoxicity), CDC (complement dependent cytotoxicity) and the like; the CH2 region has a N-linked glycosylation site N297, the glycosylation modification at this site has an important influence on the cytotoxicity of the antibody and the like, and the removal of the said glycosylation will make the antibody lose the function of inducing cytotoxicity such as ADCC. The light chain is linked to the heavy chain through the disulfide bond of the CL and the CH1 regions; the heavy chain is provided with a hinge region between CH1 and CH2 regions, which is easy to stretch and bend, and the two heavy chains of one antibody are connected via disulfide bonds in the hinge region. After the antibody is digested by papain, two Fab (fragments of antigen binding) and 1 Fc (fragment crystallizable) can be formed, wherein the Fab segment contains the complete light chain and heavy chain VH and CH1, and the Fc segment contains CH2 and CH3.

Human IgG has four subtypes: IgG1, IgG2, IgG3 and IgG4, wherein IgG1 has strong ability to induce ADCC and CDC effects and longer serum half-life, and is the most common antibody subtype of antibody drug, such as Rituximab (anti-CD20), Trastuzumab (anti-HER2); IgG 2 and IgG 4 have weaker abilities to induce ADCC and CDC effects and longer serum half-life, which can be used to develop antibody drugs whose major acting mechanisms are signal blocking, regulatory or neutralizing, such as Nivolumab (anti-PD-1), Pembrolizumab (anti-PD-1).

In order to achieve the purpose of enabling the same antibody molecule to target at two different antigens, CD47 and PD-L1, herein the antibody structure is modified, and an asymmetric fusion protein similar to an antibody structure is constructed through genetic engineering technology (FIG. 2). The fusion protein consists of a CD47 binding moiety and a PD-L1 binding moiety linked by a disulfide bond; wherein the CD47 binding moiety is formed by linking a SIRPa mutant (SIRPα-m) having a high affinity for CD47 and an antibody Fc segment (primarily CH2, CH3 region), and the PD-L1 binding moiety is formed by linking a heavy chain and a light chain of anti-PD-L1 antibody by disulfide bond.

The SIRPα mutant (SIRPα-m) in the fusion protein can bind to the CD47 antigen at much higher affinity than the endogenous natural SIRPα protein, so that the binding of the natural SIRPα on the surface of the macrophage and the CD47 antigen on the surface of cancer cells can be blocked, to avoid the inhibition and escape of cancer cells to the phagocytosis of macrophages.

The anti-PD-L1 antibody is capable of binding to PD-L1 (highly expressed on the surface of cancer cells) with high affinity, to block the binding of "PD-L1 on the surface of cancer cells to PD-1 on the surface of activated T cells, so that avoid the inhibition and escape of cancer cells to T cells.

PD-L1 is more highly expressed on cancer cell surface and the targeting property of the anti-PD-L1 is stronger, which make up the deficiencies that the CD47 specificity is poor and the anti-CD47 is severe in blood toxicity. Experiments show that the blood toxicity of the IAB is much lower than that of the fusion protein consisted of SIRPα-m and Fc, and with better safety.

The bifunctional fusion protein targeting CD47 and PD-L1 of the present disclosure serves both in early innate immunity as to activate macrophage phagocytosis of tumor cells and to improve tumor antigen presentation and in acquired immunity as to promote tumor-specific T cell activation and proliferation, while compared with a single anti-CD47 drug, with better tumor cell targeting and less blood toxicity. Animal experiments shows that the bifunctional fusion protein has better anti-tumor therapeutical effect and blood safety than anti-PD-L1 or anti-CD47 alone. And, the subject with tumor disappeared after IAB treatment can have immunity against the same type of tumor cells inoculated later.

DETAILED DESCRIPTION OF THE INVENTION

Figure 1:
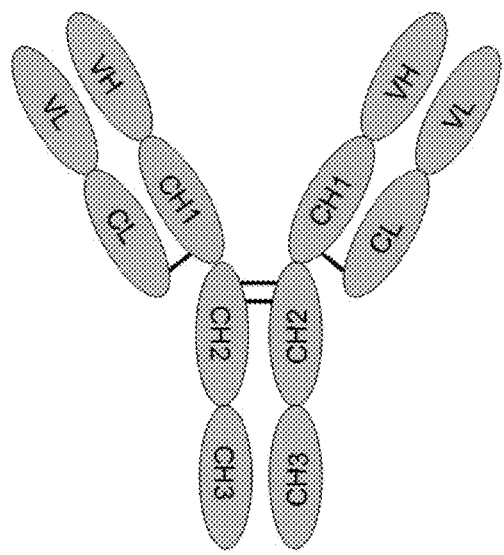
FIG. 1 is a schematic structural view of an IgG-type antibody.
Figure 2:
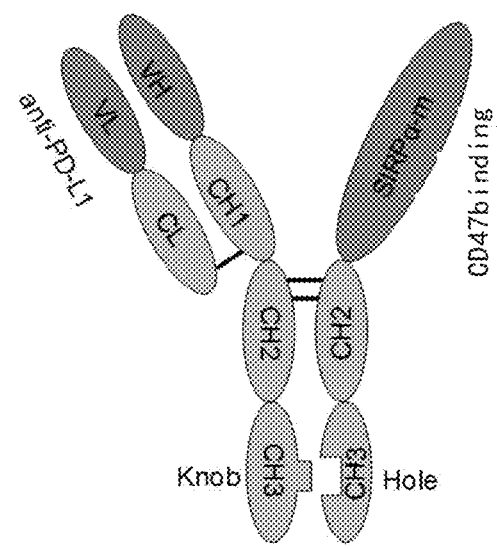
FIG. 2 is a structural schematic of the bifunctional fusion protein IAB targeting CD47 and PD-L1.

Example 1. Construction and Expression of Bifunctional Fusion Protein IAB Targeting CD47 and PD-L1

According to nucleic acids as set forth in SEQ ID NO: 4 (encoding a fusion peptide formed by linking SIRPα mutant with antibody Fc segment, with Hole structure formed by the mutation of Y349 C. T366S, L368 A and Y407 V), SEQ ID NO: 5 (encoding anti-PD-L1 antibody light chain), and SEQ ID NO: 6 (encoding anti-PD-L1 antibody heavy chain, with Knob structure formed by mutations of T366W and S354C), corresponding DNA fragments were synthesized respectively, and were inserted into the pcDNA3.1 (+) vector by genetic engineering technology. The expression vectors constructed were called as pcDNA3.1-SIRPα-m-Fc, pcDNA3.1-antiPDL1-L and pcDNA3.1-antiPDL1-H. Three expression vectors were co-transfected with liposomes into CHO-K1 host cells, and the transfected cells were cultured in DMEM complete medium containing 20% fetal bovine serum (FBS) (available from Invitrogen Inc.) for 24 hours, and then screened under pressure in selection medium containing 1 mg/ml G418, continued for incubation for 2 weeks. Subcloning screening was carried out by limited dilution assay; comparing the content of the target protein in the cell culture supernatant by Dot-Blot assay (the supernatant is blotted on a nitrocellulose membrane, and then adding a horseradish peroxidase(HRP)-labeled mouse anti-human Ig antibody, and colored by diaminobenzidine DAB after sealing), and screening a clone with the highest expression of the target protein IAB as the expression cell strain.

The expression cell strains were passaged in a mixed culture medium consisting of DMEM complete medium and CHOM-B1 serum-free medium (available from Shanghai SINOMAB biotech Ltd., Shanghai) of different ratios, and the ratio of complete medium was reduced from 100% to 0%, and then continued the culture in CHOM-B1 serum-free medium for passage. When the cell culture volume was increased to 6 L, passage was stopped, flow feeding was carried out, for which glucose was added according to 2 g/L per day, supernatant was collected after 7 days, centrifuged at 9000 rpm and 4° C. for 10 min. The precipitate was discarded, the supernatant was filtered with 0.2microfilm, and kept at 4° C. for purification.

Example 2. Purification of Bifunctional Fusion Protein IAB Targeting CD47 and PD-L1

The bifunctional fusion protein IAB was purified by Protein A affinity chromatography column method, a balance liquid of 10 times of column volume (20 mM phosphate buffer solution containing 150 mM NaCl, pH 7.0) was used for balancing the column body and then loading the supernatant. After loading, the column was washed by balance buffer of 5-10 times of the column volume to the conductance balance. Elution was then carried out with eluent (50 mM citric acid buffer, pH 3.5) and the elution peak was collected after OD 280 was greater than 200 mAU. After the eluent containing the target protein was regulated with 1M Tris to pH6.5-7.0, gel desalination column replacement buffer (pH 7.4 phosphate buffer) were used, followed by sterilizing filtration. Detected the protein concentration by UV method and stored at 4° C. for later use.

Example 3. SDS-PAGE Electrophoresis Assay of Bifunctional Fusion Proteins Targeting CD47 and PD-L1

Complete protein molecular weight and reduced molecular weight were detected by polyacrylamide gel electrophoresis (SDS-PAGE) under conditions of non-reducing (8% separating gel) and reducing (12% separating gel), respectively, by using purified antibody samples. The reagent formulation and operating method can refer to "Molecular Cloning: A laboratory Guide". The electrophoresis results are shown in FIG. 3 (non-reduced SDS-PAGE) and FIG. 4 (reduced SDS-PAGE) in the figures of the specification.

Figure 3:
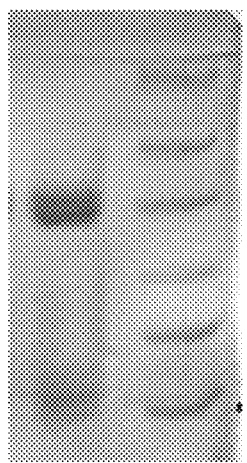
FIG. 3 is a graph of the non-reduced SDS-PAGE electrophoresis of the bifunctional fusion protein IAB targeting CD47 and PD-L1.
Figure 4:
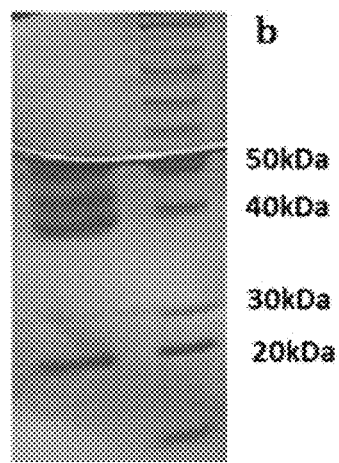
FIG. 4 is a graph of the reduced SDS-PAGE electrophoresis of the bifunctional fusion protein IAB targeting CD47 and PD-L1.

In the non-reduced SDS-PAGE electrophoresis diagram of FIG. 3, the complete protein molecular weight of the target protein IAB was about 120 kDa; in the reduced SDS-PAGE electrophoresis diagram of FIG. 4, the partial molecular weight of the heavy chain of the IAB protein (anti-PDL1-H) was about 50 kDa, and the fusion peptide chain (SIRPα-m-Fc) has a partial molecular weight of about 40 kDa, the light chain (anti-PDL1-L) moiety was 25 kDa, which is substantially consistent with the theoretical value. The fusion peptide chain (SIRPα-m-Fc) in FIG. 4 exhibits two bands of about 40 kD, which may be associated with the effect of post-translational modifications and spatial structure on electrophoresis.

Example 4. Determination of IAB Complete Protein Molecular Weight and Major Sugar Type by Liquid Phase Chromatography Tandem Mass Spectrometry Assay The expressed and purified IAB fusion protein was desalted into 50 mM $NH_4HCO_3$ solution, and the desalted protein solution was quantified by UV (50 mM $NH_4HCO_3$ as blank control with an extinction coefficient of 1.60). The desalted protein solution was added to 50 mM $NH_4HCO_3$, diluted to 1 mg/mL for loading.

Liquid chromatography conditions: Liquid Phase Equipment, Waters ACQUITY UPLC system; chromatographic measures: BEH 300.4 C4 1.7 μm, 2.1×50 mm; column temperature 60° C.; sample chamber temperature 15° C.; flow rate 0.4 ml/min; mobile phase A: 99.9% water+0.1% formic acid; mobile phase B: 99.9% acetonitrile+0.1% formic acid; loading volume: 5 μL; detector ESI-Q-TOF.

Mass spectrum conditions: mass spectrometry equipment: Waters; source temperature 120; capillary voltage setting: 3000V; primary cone voltage setting: 40 V; secondary cone voltage setting: 4V; cone gas flow rate: 50 L/H; acquisition time range 3-15 min; desolvation temperature setting: 400° C. quality calibration range selection: 500-3000 m/z; acquisition quality range selection 500-3000 m/z; scan time: 1.0 S.

Figure 5:
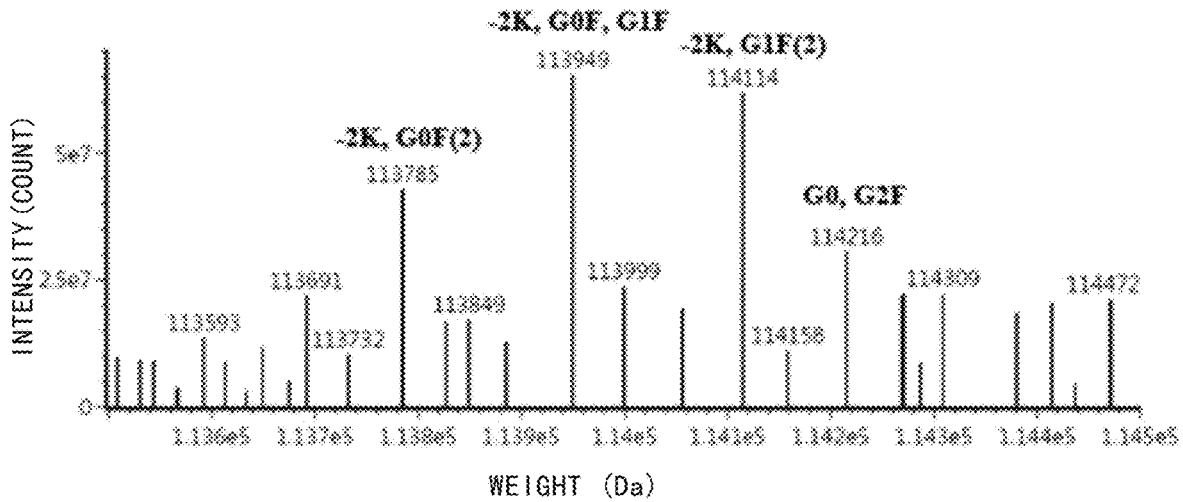
FIG. 5 is the mass spectrometry determining the IAB complete protein molecular weight and major sugar types.

The results are shown in FIG. 5. The main sugar types modified after IAB translation are -2KG0F(2)(molecular weight 113785), -2KG0FG1F (molecular weight 113949), -2KG1F(2)(molecular weight 114114), G0G2F (114216), without significant production of undesirable sugar types. Its molecular weight and theoretical molecular weight (post-translational modification) are consistent.

Example 5. Preparation and Identification of Control SIRPα-m-Fc' and Anti-PDL1'

According to nucleotide sequences of SEQ ID NO:9 (encoding the fusion peptide formed by linking SIRPα high affinity mutant SIRPα-m and IgG1 antibody Fc, but without "Hole" structure) and SEQ ID NO: 10 (encoding heavy chain of anti-PD-L1 antibody, but without "Knob" structure, and the Fc glycosyl modification was removed by N297A mutation), corresponding DNA fragments were synthesized, and inserted into the pcDNA3.1 vector respectively to construct expression vectors pcDNA3.1-SIRPα-m-Fc' and pcDNA3.1-antiPDL1-H '.

The pcDNA3.1-SIRPα-m-Fc' was transfected into CHO-K1 expression host cells according to the method of Example 1. The strains of high expression were screened, and the control SIRPα-m-Fc fusion protein was prepared by using the protein expression and purification methods in Examples 1 and 2, and the protein was named as SIRPα-m-Fc' with the amino acid sequence as set forth in SEQ ID NO: 7.

A control anti-PD-L1 antibody was prepared by co-transfect pcDNA3.1-antiPDL1-H' and pcDNA3.1-antiPDL1-L prepared in Example 1 into CHO-K1 expression host cell and screen cell strain with high expression. Protein expression and purification method in Examples 1 and 2 was used to prepare said control antiPD-L1 antibody, which was called anti-PDL1' with the amino acid sequence as set forth in SEQ ID NO: 8.

Example 6. Determination of Antigen Binding Ability of IAB Fusion Protein (1) The Determination of the Binding Ability of IAB to Human PD-L1 by Competitive ELISA Biotin labeled anti-PDL1' was used. The recombinant expressed human PD-L1-Fc fusion protein was diluted with 0.1M $NaHCO_3$ solution (pH9.6) to 5 μg/ml and coated the microwell plates at 100 μl/well, washed, blocked, and then biotin-labeled anti-PDL1' and gradient diluted competitors were added into each well, wherein the competitors were unlabeled anti-PDL1' or IAB proteins prepared in Example 2. The competitor concentrations were respectively initiated from 1 μg/ml, and 2-fold diluted. Each concentration was repeated in triplicate wells, incubated at 37° C. for 1 hour, and then the reaction liquid was discarded, plates were washed. Avidin-labeled horseradish peroxidase (Avidin-HRP) and substrate TMB were added for developing, OD450 nm absorbence was measured. The results were plotted and shown in FIG. 6. The x axis is competitor concentration (ng/ml) and the y axis is OD value, hollow triangle is competition data of anti-PDL1', and the solid circle is competition data of IAB.

TABLE 1

Competitive ELISA Assay Results of IAB Fusion Protein and anti-PDL1'

|  | Parameter | Estimated value | S.D | Confidence interval |
|---|---|---|---|---|
| Result of anti-PDL1' | A | 2.119 | 0.019 | [2.080, 2.158] |
| competitive binding | B | 0.939 | 0.024 | [0.889, 0.989] |
| $R^2 = 0.999$ | C | 0.948 | 0.029 | [0.889, 1.007] |
| IC50 = 0.948 | D | 0.001 | 0.010 | [−0.019, 0.021] |
| Result of IAB competitive | A | 1.999 | 0.011 | [1.976, 2.022] |
| binding | B | 0.912 | 0.028 | [0.854, 0.970] |
| $R^2 = 0.999$ | C | 11.76 | 0.425 | [10.89, 12.63] |
| IC50 = 11.76 | D | −0.028 | 0.020 | [−0.069, 0.014] |

(2) The Binding Ability of IAB with Human CD47 Determined by Competitive ELISA

The binding of IAB protein to CD47 was determined by the same method, The antigen coating microwell plate was a recombinant expressed human CD47 protein, Biotin-labeled SIRPα-m-Fc' and gradient diluted competitors were added. The competitors were unlabeled SIRPα-m-Fc' or IAB proteins prepared in Example 2. The competitor concentrations were respectively initiated from 1 μg/ml, and 2-fold diluted. Each concentration was repeated in triplicate wells, after incubation, horseradish and TMB were used for developing, OD450 nm absorbance was measured. The results were plotted and shown in FIG. 7. The x axis is competitor concentration (ng/ml) and the y axis is OD value, hollow triangle is competition data of anti-PDL1', and the solid circle is competition data of IAB.

TABLE 2

Competitive ELISA Assay Results of IAB fusion protein with SIRPα-m-Fc'

|  | Parameter | Estimated value | S.D | Confidence interval |
|---|---|---|---|---|
| Results of SIRPα-m- | A | 1.166 | 0.015 | [1.136, 1.196] |
| Fc' competitive binding | B | 1.770 | 0.105 | [1.554, 1.987] |
| $R^2 = 0.996$ | C | 0.918 | 0.035 | [0.846, 0.991] |
| IC50 = 0.918 | D | 0.007 | 0.009 | [−0.011, 0.026] |
| Results of IAB | A | 1.154 | 0.011 | [1.131, 1.177] |
| competitive binding | B | 1.513 | 0.078 | [1.352, 1.673] |
| $R^2 = 0.997$ | C | 2.897 | 0.111 | [2.688, 3.127] |
| IC50 = 2.897 | D | 0.013 | 0.010 | [−0.008, 0.033] |

Figure 6:
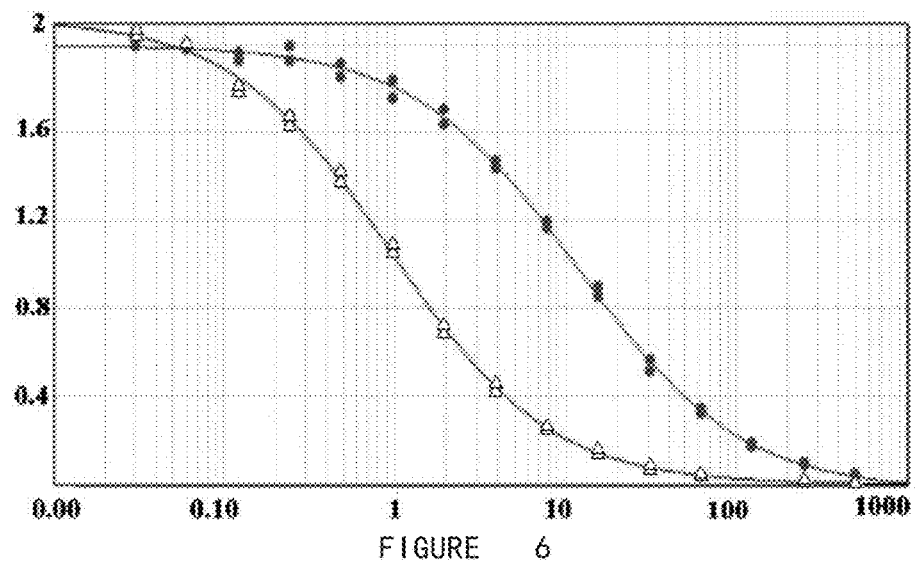
FIG. 6 shows IAB fusion protein and monospecific anti-PD-L1 antibody anti-PDL1' competitively combine PD-L1.
Figure 7:
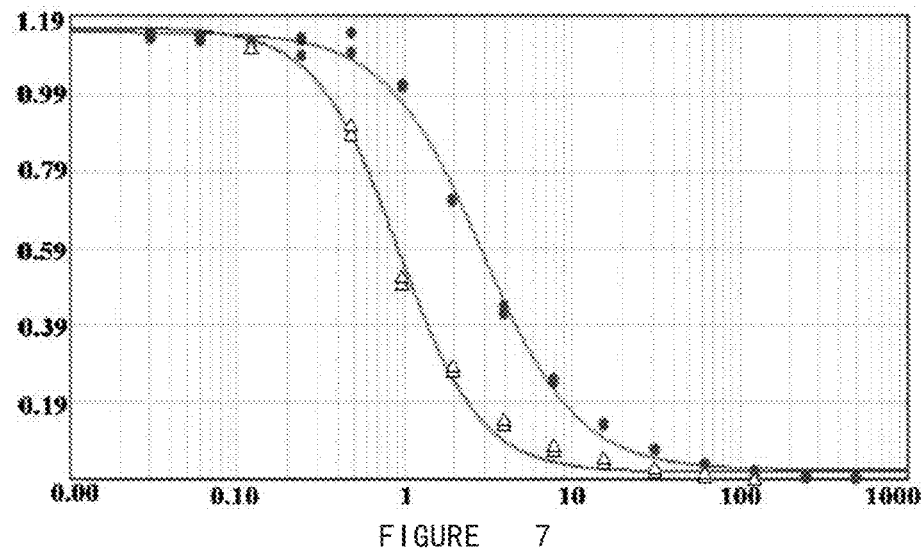
FIG. 7 shows IAB fusion protein and SIRPα high affinity mutant Fc fusion protein competitively combine CD47.

The results of FIGS. 6 and 7 illustrate that fusion protein IAB has binding activity to both target antigens PD-L1 and CD47 at the same time and recognizes the same binding epitope as prototype antibody or ligand, having competitive binding capacity. However, since the IAB protein and binding site are "monovalent", its affinity is reduced compared to the prototype antibody or ligand. The affinity of IAB (IC50=11.76) to PD-L1 was reduced by nearly 10 times compared to the affinity of PD-L1' (IC 50=0.948); and the affinity of IAB to CD47 (IC50=2.897) was reduced by approximately 3 times compared to the affinity of SIRPα-m-Fc' (IC50=0.918).

(3) Flow Cytometry Assay for Binding Ability of IAB Protein to Cancer Cells

Figure 19:
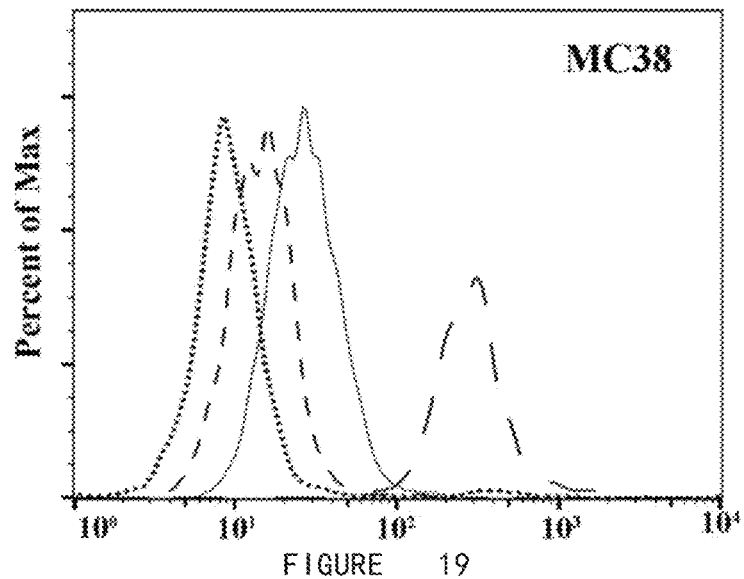
FIG. 19 shows that flow cytometry detects the binding capacity of MC 38 tumor cells to IAB proteins.
Figure 20:
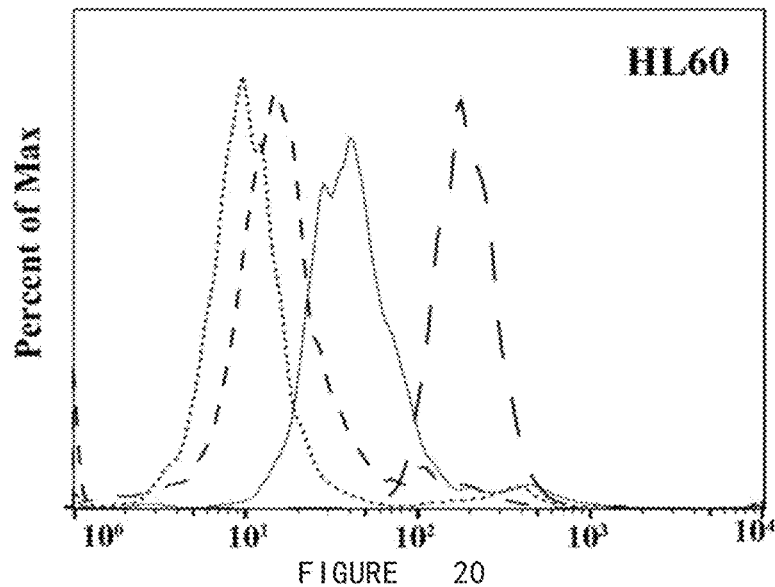
FIG. 20 shows that flow cytometry detects the binding capacity of HL 60 leukemia cells to IAB protein.

The binding of IAB protein to MC38 cells (mouse colon cancer cells), HL60 cells (human leukemia cells) was detected using flow cytometry and the results are shown in FIGS. 19 and 20 (dotted lines represent blank controls, and solid lines represent IAB proteins, short, dashed lines represent anti-PDL1', and long dashed lines represent SIRPα-m-Fc') using SIRPα-m-Fc' and anti-PDL1' as control. The results illustrate that the IAB protein can bind to the surface of MC38 cell and the HL60 cells.

Figure 8:
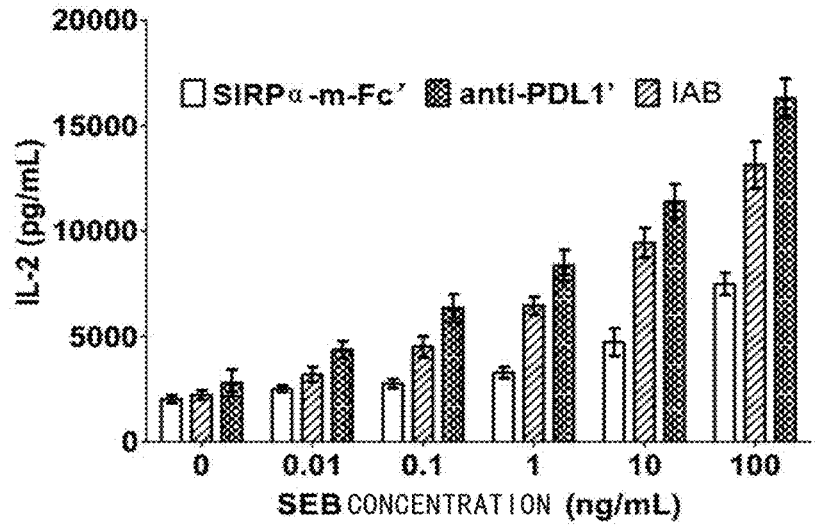
FIG. 8 shows IAB fusion protein enhances the release of IL-2 by PBMC cells stimulated by SEB.

Example 7. Study of Bifunctional Fusion Protein IAB Targeting CD47 and PD-L1 Mediated T-Cell Activation 20 ml of healthy human venous blood is collected and density gradient centrifuge was used to separate peripheral blood mononuclear cells (PBMC). PBMC was re-suspended in RPMI 1640 medium containing 10% FBS, plated onto 96-well cell culture platesat $1 \times 10^5$ cells/well and then added to each well RPMI1640 medium comprising different concentrations (0.01 ng/ml, 0.1 ng/mL, 1 ng/mL, 10 ng/ml, 100 ng/ml) Staphylococcus enterotoxin B (SEB) and 20 μg/ml associated protein (IAB, anti-PDL1' or SIRPα-m-Fc'), incubated for 72 h in 37° C., 5% CO2 incubator. The cell status was observed by an inverted microscope on a daily basis. The supernatant was taken after 72 hours, and the amount of IL-2 secretion was determined by ELISA. Experimental results are shown in FIG. 8. The stimulation of PBMC cells by SEB can increases its IL-2 secretion amount and exhibits a dose-dependent profile within a certain concentration range of SEB (0–100 ng/mL). The IL-2 amount of IAB and anti-PDL 1' groups at different SEB concentrations are significantly higher than SIRPα-m-Fc'. It is proved that the IAB can activate T cells in vitro.

Example 8. Study of the Phagocytosis of Raw 264.7 In Vitro Mediated by Bifunctional Fusion Protein IAB Targeting CD47 and PD-L1

$2 \times 10^6$ mouse colon cancer cell strain MC 38 was incubated with 2000 μL of 5 μM CSFE (2-carboxyfluorescein diacetate succinimidyl ester, a live fluorescent dye) solution at 37° C. for 20 min, and then 10 mL of complete medium was added, incubated for 5 min to remove unbound CSFE in the solution. The marked tumor cells were collected by centrifugation and resuspended in complete medium to prepare tumor cell suspension at a concentration of $1\times10^6$/mL.

1 ml of $5\times10^4$ cell/ml mouse macrophage RAW264.7 (ATCC TIB-71) suspension was added to each well in a 24-well plate. After the macrophages were attached to the wall, the culture medium in the well plate was discarded, and then serum-free culture medium was added for incubation for 2 hours. Then, CFSE-labeled tumor cells ($2\times10^5$) were added into each well, while adding IAB protein, control SIRPα-m-Fc', anti-PDL1', i.v. human immunoglobulin (IgG1, available from China Biologic Products Holdings, Inc.) at final concentration of 10 µg/ml, incubated at 37° C. for 2 h.

Macrophages were digested with Trypsin and then collected by centrifugation, washed twice with PBS. After counted on Hemocytometer, the cell density was adjusted to $1\times10^6$/mL and resuspended in PBS buffer containing 1% FBS. Cell suspension was then added to flow cytometry assay tube (100 µL/tube), centrifuged to discard supernatant, and 100 µL of fluorescent labeled antibody (PE-labeled anti-mouse F4/80 antibody) was added to the flow cytometry tube, incubated on ice in dark for 45 min, washed twice with PBS buffer containing 1% FBS and assay in the suspension in 300 µl PBS. PE mono-positive was macrophages, CSFE mono-positive was MC38 tumor cells, PE and CSFE double-positive cells were macrophages for phagocytosis of MC38 cells. Phagocytosis rates of macrophages under the action of different proteins were calculated.

Figure 9:
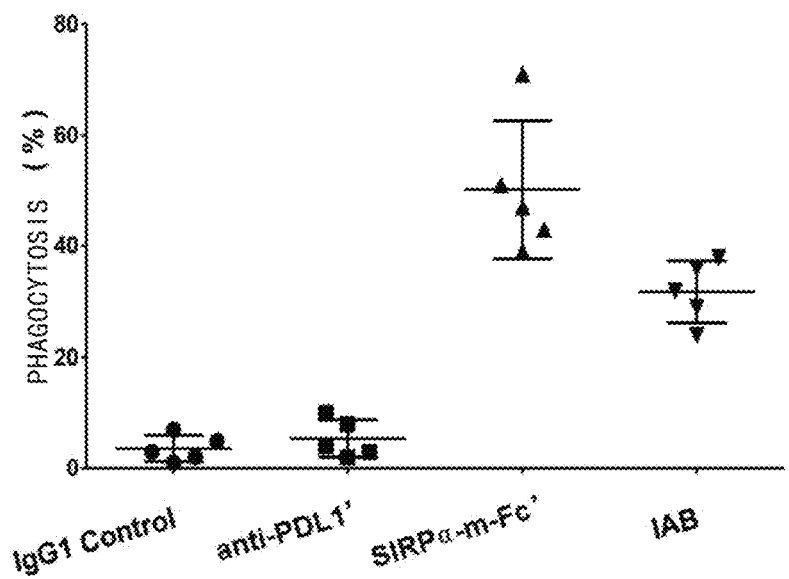
FIG. 9 shows flow cytometry to determine that IAB fusion protein promotes the phagocytosis of MC38 cells in vitro by RAW264.7.

The experimental results are shown in FIG. 9. In macrophage-tumor cell co-culture system, the macrophage phagocytosis efficiency in the co-culture system is substantially the same (<10%) when comparing anti-PDL1' to the negative control (IgG1). While for positive control (SIRPα-m-Fc') and IAB fusion protein, the phagocytosis efficiency of macrophages in the co-culture system can be greatly improved, wherein the phagocytosis promoting ability of the IAB fusion protein (36%) is lower than SIRPα-m-Fc' (49%), while anti-PDL1' does not have the ability to promote the macrophage phagocytosis.

Figure 10:
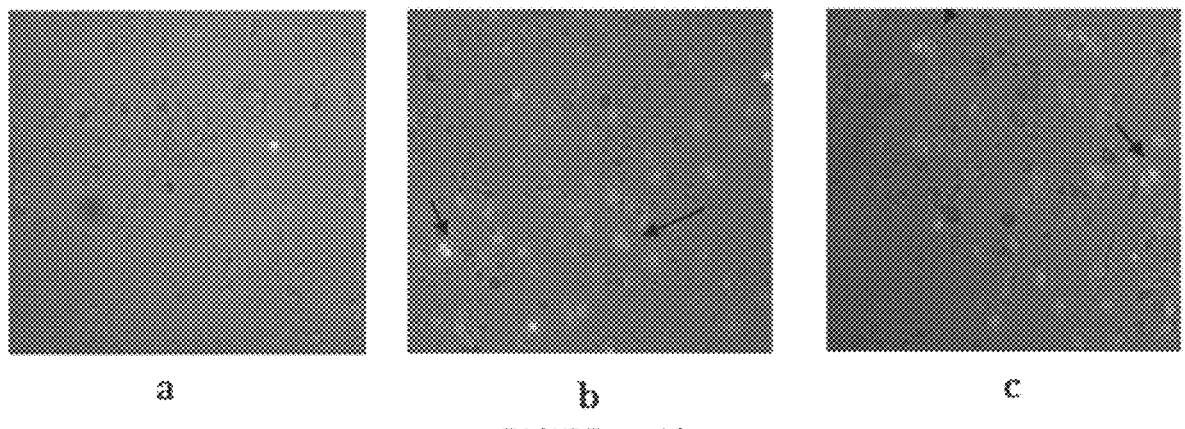
FIG. 10a-c show fluorescence microscopy to determine that IAB fusion protein promotes the phagocytosis of MC38 cells by mouse myeloid-derived macrophages.

To further verify the phagocytosis promoting ability of IAB fusion protein on macrophages derived from mouse myeloid, mouse myeloid cells were isolated and cultured for 7-10 days with the induction of 50 ng/ml M-CSF to prepare mouse myeloid-derived macrophages. $5\times10^4$ mouse myeloid-derived macrophages were mixed with $2\times10^5$ CFSE-labeled MC38 tumor cells, adding into IAB fusion protein, negative control (IgG1) and positive control SIRPα-m-Fc', incubated at 37° C. for 2 hours, photographed with an inverted microscope, and macrophages with green fluorescence in the image were macrophages after phagocytosis of tumor cells. As shown in FIG. 10, macrophages (FIG. 10a) adhere to the wall and stretch out the pseudopods in the negative control group added with IgG1 (FIG. 10a), almost no macrophages phagocytized tumor cells (green fluorescence). In IAB combination (FIG. 10c) and positive control group SIRPα-m-Fc' (FIG. 10b), the macrophages phagocytized tumor cells (green fluorescence) (indicated by the black arrows). The above results again verify that the IAB fusion protein has the ability to promote macrophage phagocytosis of tumor cells in vitro.

Example 9. ADCC Reporter Gene Experiments

Figure 11:
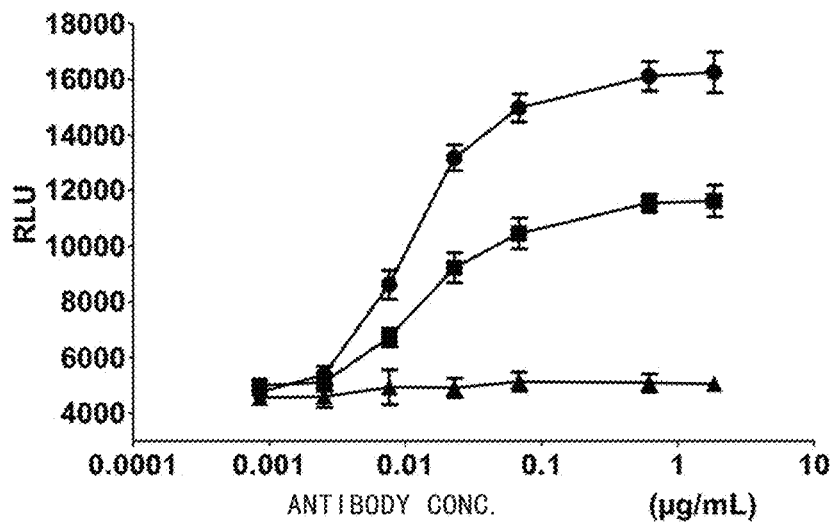
FIG. 11 shows the ADCC effect of IAB fusion protein determined by indicator cell culturing method.

Different concentrations of antibodies to be tested (IAB fusion protein, positive control SIRPα-m-Fc', negative control anti-PDL1') were incubated with Jurkat cells (effector cells) expressing FcγIIIa transformed by luciferase reporter gene and MC38 tumor cells (target cells), incubated at 37° C. in an incubator with 8% CO2 for 4 h; the fluorescent substrate was added, Fluorescence readings were measured on Glomax®well plate fluorescence assay ELISA, and the results are shown in FIG. 11.

The black squares in FIG. 11 are data for IAB fusion proteins. The black solid circles are the data of SIRPα-m-Fc', and the black triangles are the data of anti-PDL1'. The data illustrated that the IAB fusion protein has certain ADCC effect, but the ADCC effect thereof at equivalent doses is lower than that of SIRPα-m-Fc', possibly in relation to the Knob-in-Hole structure. Because of the introduction of N297A mutation into the conservative glycosylation site in antibody Fc segment and without glycosyl modification, the ADCC effect is lost.

Example 10. Blood Toxicity Assay of Bifunctional Fusion Protein IAB Targeting CD47 and PD-L1

Figure 12:
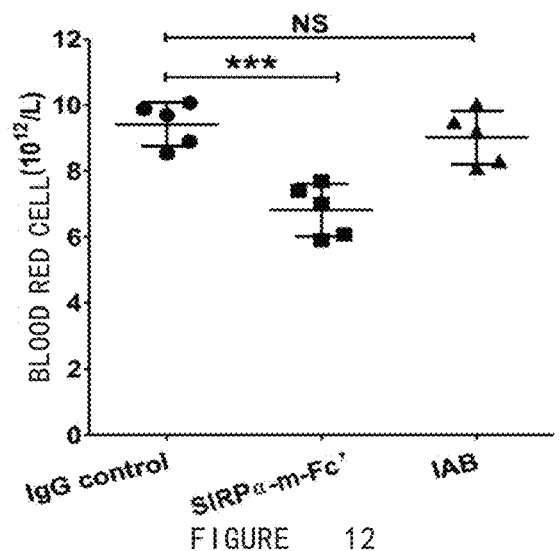
FIG. 12 is the blood red cell content in serum of mice following intraperitoneal injection of 100 mg/kg of drug.
Figure 13:
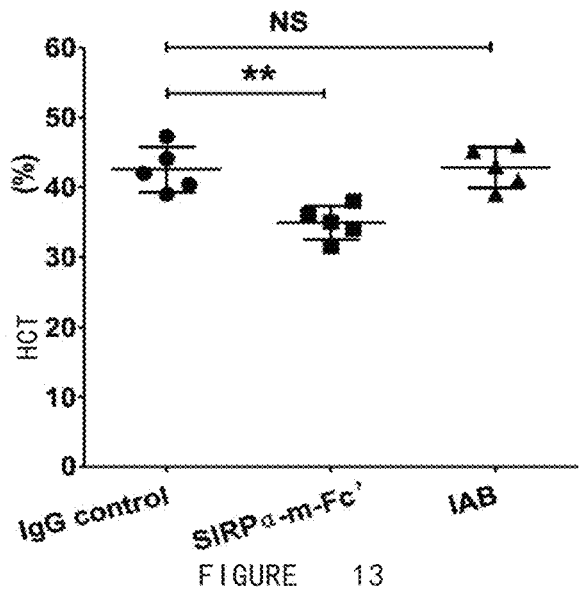
FIG. 13 is the hematocrit in the blood of mice following intraperitoneal injection of 100 mg/kg of drug.
Figure 14:
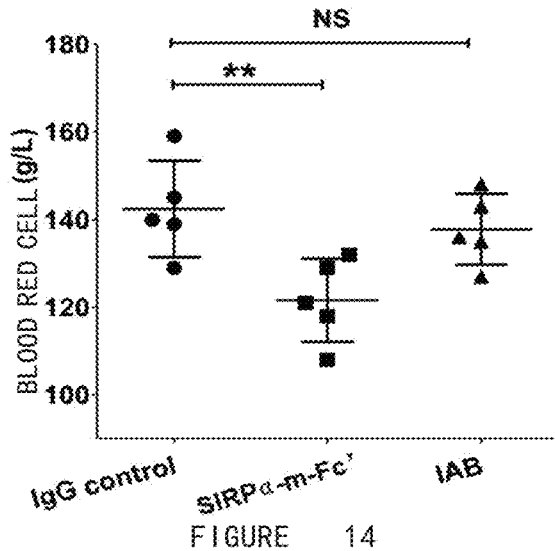
FIG. 14 shows the hemoglobin content in the blood of mice following intraperitoneal injection of 100 mg/kg of drug.

15 healthy Balb/c mice (6–8 weeks) were randomly divided into 3 groups (5 per group) by weight (on average about 20 g). Each group of mice were administered intraperitoneally (IAB, SIRPα-m-Fc', or i.v. human IgG) at a dose of 100 mg/kg; after 24 hours of administration, mice were sampled for blood through the orbital about 500 µl into EP tube, and 1% heparin sodium 10 µL was added immediately to prevent clotting. Mouse blood analysis was performed at Shanghai Model Organisms Center, Inc. By monitoring the change of indexes such as red blood cells, blood proteins, red blood cell specific volume, platelets and the like in mice blood after administration, blood toxicity of prototype antibody and IAB fusion protein were evaluated, and the results are shown in FIG. 12, FIG. 13, and FIG. 14. The results suggest that red blood cell content ($9.1\times10^{12}$/L), HCT (43.0%), hemoglobin (137.8 g/L) of the experimental group injected with IAB protein do not have significant difference from the red blood cell content ($9.4\times10^{12}$/L), HCT (42.56%), and hemoglobin (142.4 g/L) of the control group injected with human IgG. Whereas the group injected with SIRPα-m-Fc' was affected by the blood toxicity, the relevant data are red blood cell content $8\times10^{12}$/L, HCT 35.07%, and hemoglobin 121.6 g/L, which are significantly different from the other two groups.

Figure 15:
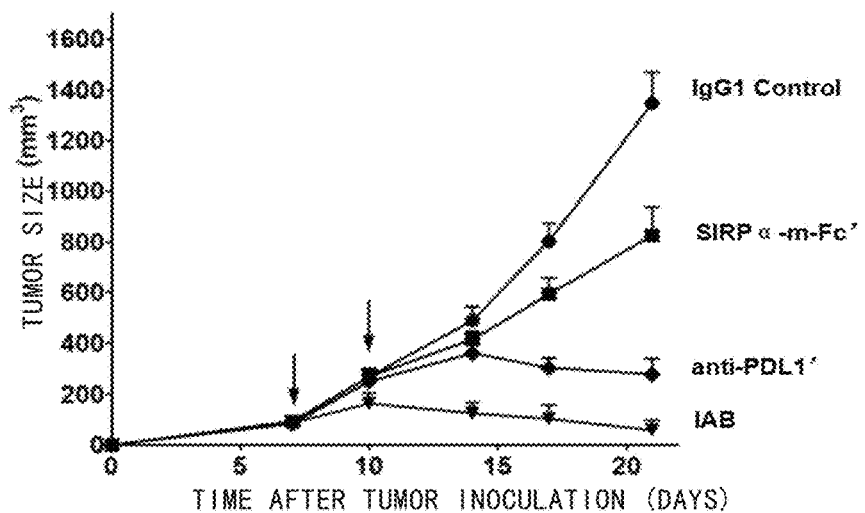
FIG. 15 shows experimental results for the IAB fusion protein treatment of Balb/c Mice MC38 Tumor Model.

Example 11. Study of Tumor Inhibition Activity of Bifunctional Fusion Protein IAB Targeting CD47 and PD-L1 in Mice (1) The IAB Treatment of Balb/c Mice MC38 Tumor Model:
Balb/c female mice (6–8 weeks) were inoculated with MC38 tumor cells ($2\times10^5$cells/animal) subcutaneously, total 40 mice. After removing mice with too large or too small tumors on day 6, the remaining mice were grouped into 4 groups according to the tumor volume (about 100 mm³), each group 8 mice. IAB fusion protein, irrelevant control (human IgG1), or the prototype antibody (SIRPα-m-Fc', anti-PDL1') were injected into the tumor at 10 mg/kg. Tumor formation in mice were observed twice a week, using calipers to measure the maximum diameter (length) and the vertical distance (width) of the tumor, with the calculation formula for tumor volume: volume=0.5×length×width². When the tumor volume in mice was greater than 2000 mm³, or large area of ulcer appeared at the tumor site, the mice were sacrificed by cervical dislocation. The observation usually lasts 21 days. The experimental results are shown in FIG. 15.

The experimental results show that after the control group was administered with irrelevant antibodies (i.v. human IgG1), the tumor was in progressive growth, and the average volume of tumor on day 21 reached 1472 mm$^3$ at the end of observation (21 days after inoculation), the control group and the SIRPα-m-Fc' treatment group mice were dispirited, thin, wrinkled skin and with slow movement. The tumor on the back of the anti-PDL1' and IAB treatment group mice were shrunk to various extent. The average tumor size of anti-PDL1' treatment group mice is 289 mm$^3$. The average tumor size of IAB treatment group mice is 67 mm$^3$, and tumor in some of the mice completely disappeared, indicating that IAB fusion protein has better anti-tumor effect than prototype protein (anti-PDL1' and SIRPα-m-Fc') in the treatment of MC38 tumor model. The tumor suppressing effect is with the following order: IAB>anti-PDL1'>SIRPα-m-Fc'. The result shows that under same dosage and with same administration route, the IAB fusion protein has a "synergistic effect" of tumor suppression.

Figure 16:
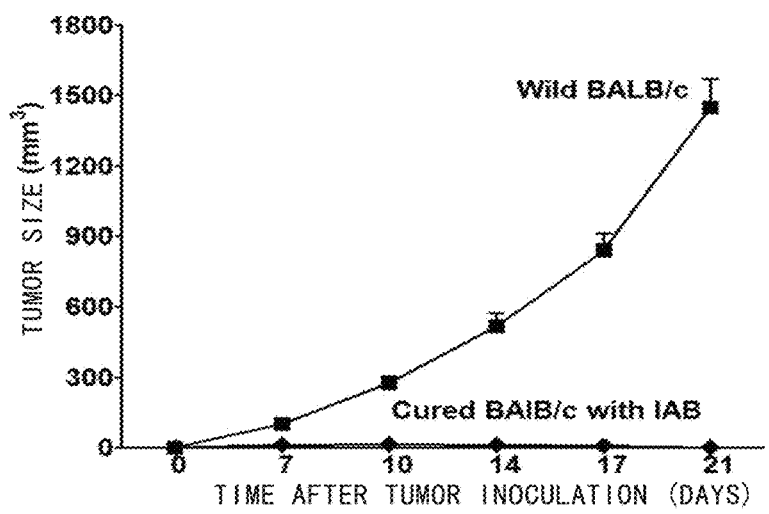
FIG. 16 shows experimental results of the prevention by IAB fusion protein on the Balb/C mice inoculated twice with MC38 tumor cells.

(2) IAB Prevent Tumor in the Balb/c Mice Inoculated with MC38 Tumor Model (Secondary Inoculating):

Mice treated with IAB fusion protein treatment groups whose tumor completely disappeared (touching inoculation sites with no accessible tumors) and healthy BALB/c mice were subjected to MC38 secondary inoculation experiment. MC38 tumor cells were inoculated subcutaneously on the other side of the primary inoculation site in mice, with the inoculum size of 2×10$^5$ cells/animal. Tumor formation in mice were observed twice a week, using calipers to measure the maximum diameter (length) and the vertical distance (width) of the tumor, with the calculation formula for tumor volume: volume=0.5×length×width$^2$. When the tumor volume in mice was greater than 2000 mm$^3$, or large area of ulcer appeared at the tumor site, the mice were sacrificed by cervical dislocation. The observation usually lasts 21 days. The experimental results are shown in FIG. 16.

The experimental results showed that after the control group (healthy Balb/c mice) was inoculated with MC38 cells, the tumor was in progressive growth, and the average volume of tumor on day 21 reached 1453 mm$^3$; however, after the mice cured with IAB fusion protein were inoculated with MC38, no accessible tumor (less than 30 mm$^3$) can be found at the inoculation site within 21 days. Only one mouse had evidence of tumor growth on day 10, but disappeared itself later. The above results showed that it is possible that the cured mice have alleviate the tumor adaptability for MC38 and the inhibitory state of innate immunity, and the antigen-specific T cells generated after the adaptive immune activation can inhibit the tumor formation of the MC38 tumor cells for a second time.

Example 12. Acting Mechanism Studies of Bifunctional Fusion Protein IAB Targeting CD47 and PD-L1

Figure 17:
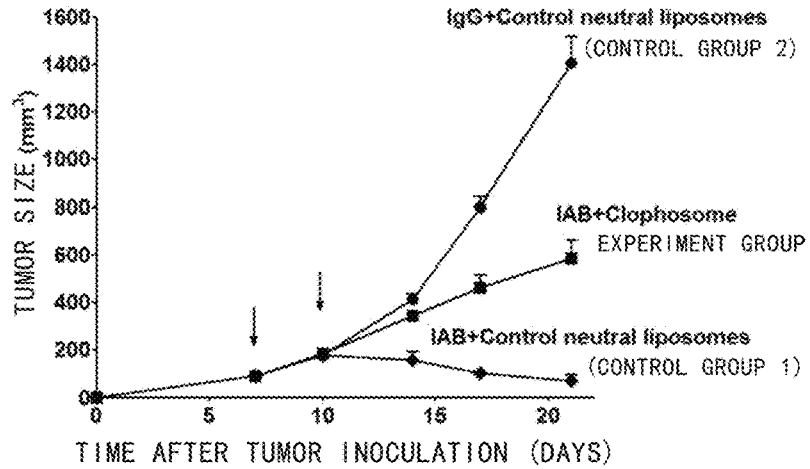
FIG. 17 shows experimental results of the IAB Treatment of MC38 Tumor-Bearing Mice (Macrophage Defect Type).

(1) IAB Treatment for MC38 Tumor-Bearing Mice (Macrophage Defective Type):

MC38 tumor cells were inoculated subcutaneously to 15 BALB/C healthy female mice of 6–8 weeks at 2×10$^5$ cells. On day 6, mice were grouped according to the mean tumor volume into three groups, each group consisting of 5 mice, and assigned as experimental group, control group 1, and control group 2. Experimental group were injected with Clophosome (a macrophage remover, available from Shanghai BangLv Biotech Co., Ltd) at 200 μL/mouse, then 100 μL/mouse every other day; IAB fusion protein were injected into the tumor at 10 mg/kg dose on day 7 and day 10. Control group 1 were injected with blank liposome instead of Clophosome to inject mouse, and IAB fusion protein were injected into the tumor at 10 mg/kg dose on day 7 and day 10; Control Group 2 were injected with blank liposome instead of Clophosome, and irrelevant human IgG antibody was injected into the tumor at 10 mg/kg dose on day 7 and day 10. Tumor formation in mice were observed twice a week, using calipers to measure the maximum diameter (length) and the vertical distance (width) of the tumor, with the calculation formula for tumor volume: volume=0.5×length×width$^2$. When the tumor volume in mice was greater than 2000 mm$^3$, or large area of ulcer appeared at the tumor site, the mice were sacrificed by cervical dislocation. The observation usually lasts 21 days. The experimental results are shown in FIG. 17.

The experimental results show that after the mice without removal of macrophages were injected with irrelevant antibodies (that is, control group 2), the subcutaneous tumor was in progressive growth, and the average volume of tumor on day 20 reached 1419 mm$^3$. After administration of IAB fusion protein (that is, the control group 1), the tumor in the mice without removal of macrophages was effectively inhibited, the average size of tumor on day 20 was only 55.8 mm$^3$. After IAB fusion protein administration, the mice with removal of macrophage (that is, the experimental group) although have partly inhibited tumor growth, and the average tumor size on day 21 is 587 mm$^3$, the tumor inhibitory effect is significantly lower than the healthy mice group (control group 1). The above experiment suggests that the in vivo tumor inhibitory effect of IAB fusion protein depends on the innate immune cells (Macrophages).

(2) Treatment of MC38 Tumor Bearing Mouse (CD8+ T Cell Defective Type) by IAB:

Each BALB/c mouse was injected twice weekly with anti-CD8 antibodies or irrelevant IgG antibodies (200 μg/mouse/time) to remove CD8+ positive T cells in mice.

Figure 18:
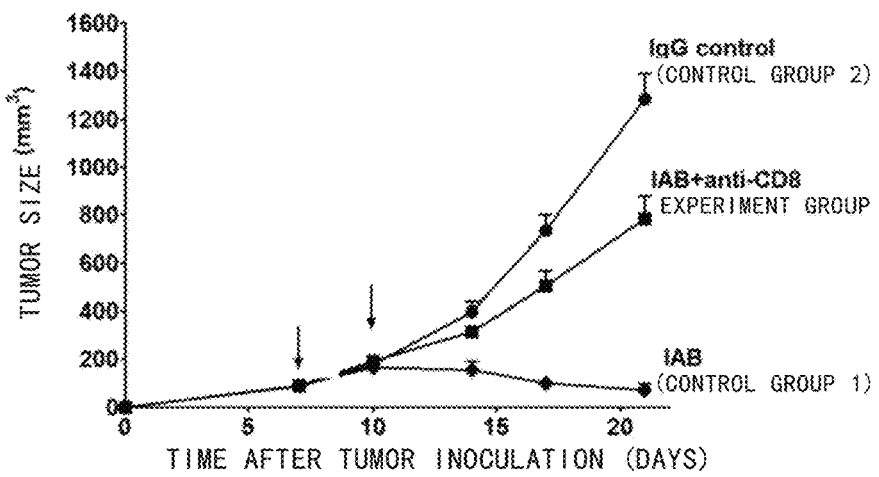
FIG. 18 shows experimental results of the IAB treatment on MC38 tumor-bearing mice (CD8+ T cell defect type).

MC38 tumor cells were inoculated subcutaneously to 5 Balb/c mice with the removal of CD8+ T cells (experimental group), 10 healthy female mice (divided into control groups 1 and 2) of 6–8 weeks at 2×10$^5$ cells. On day 6, experimental group and control group 1 were injected with IAB fusion protein in tumor at 10 mg/kg dose on day 7 and day 10. Control group 2 was injected with irrelevant human IgG antibodies at 10 mg/kg dose in tumor on day 7 and day 10. Tumor formation in mice were observed twice a week, using calipers to measure the maximum diameter (length) and the vertical distance (width) of the tumor, with the calculation formula for tumor volume: volume=0.5×length×width$^2$. When the tumor volume in mice was greater than 2000 mm$^3$, or large area of ulcer appeared at the tumor site, the mice were sacrificed by cervical dislocation. The observation usually lasts 21 days. The experimental results are shown in FIG. 18.

In the experimental results, after the irrelevant antibody was administered to the mice without removal of CD8+ T cells, the MC38 tumor size was in progressive increase, and the average volume of tumor on day 21 reached 1269 mm$^3$. After IAB fusion protein was administrated to the mice without removal of CD8+ T cells (control group 1), the tumor was effectively inhibited, the average volume of tumor on day 21 was only 64.9 mm$^3$. After the administration of IAB fusion protein, the mice with removal of CD8+ T cells (the experimental group) have average tumor volume of 777 mm$^3$ on day 21, whose tumor inhibitory effect is significantly lower than the healthy mice IAB administration group (Experimental group). The above experiment results suggest that the in vivo tumor inhibitory effect of IAB fusion protein also depends on the adaptive immune cells (CD8+ T cells).

The invention claimed is:

1. A bifunctional protein, characterized in that the bifunctional protein consists of two moieties linked by disulfide bonds,
   wherein one moiety is a CD47 binding moiety formed by linking SIRPα mutant to an antibody Fc, and the other moiety is a Programmed death-ligand 1 (PD-L1) binding moiety formed by linking a light chain and a heavy chain of anti-PD-L1 antibody by disulfide bond, the PD-L1 binding moiety having a Fc segment;
   wherein the bifunctional protein has a Knob-in-Hole structure formed by the CD47 binding moiety and the PD-L1 binding moiety, the Fc of the CD47 binding moiety has four amino acid mutations of y349c, t366s, l368a and y407v, and the Fc segment of the PD-L1 binding moiety has two amino acid mutations of t366w and s354c; and
   wherein the CD47 binding moiety comprises SEQ ID NO: 1, the light chain of the PD-L1 binding moiety comprises SEQ ID NO: 2, and the heavy chain comprises in SEQ ID NO: 3.

2. A method for treating a tumor comprising: administrating the bifunctional protein of claim 1 to a subject with the tumor.

* * * * *